United States Patent
Dubovoy et al.

(10) Patent No.: US 10,111,817 B2
(45) Date of Patent: Oct. 30, 2018

(54) ANTIPERSPIRANT COMPOSITIONS CONTAINING ETHYLENEDIAMINE DISUCCINATE

(71) Applicant: Colgate-Palmolive Company, New York, NY (US)

(72) Inventors: Viktor Dubovoy, Cresskill, NJ (US); Richard Adams, South Orange, NJ (US); Sandra Wadeer, Flanders, NJ (US); Christine Boyke, Somerset, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/327,833

(22) PCT Filed: Jul. 21, 2014

(86) PCT No.: PCT/US2014/047347
§ 371 (c)(1),
(2) Date: Jan. 20, 2017

(87) PCT Pub. No.: WO2016/014011
PCT Pub. Date: Jan. 28, 2016

(65) Prior Publication Data
US 2017/0202761 A1    Jul. 20, 2017

(51) Int. Cl.
*A61K 8/41* (2006.01)
*A61K 8/26* (2006.01)
*A61Q 15/00* (2006.01)

(52) U.S. Cl.
CPC ............ *A61K 8/41* (2013.01); *A61K 8/26* (2013.01); *A61Q 15/00* (2013.01); *A61K 2800/874* (2013.01)

(58) Field of Classification Search
None
See application file for complete search history.

(56) References Cited

U.S. PATENT DOCUMENTS

| | | | |
|---|---|---|---|
| 6,375,937 B1 | 4/2002 | Chopra et al. | |
| 6,485,716 B1 | 11/2002 | Fei et al. | |
| 6,495,097 B1 | 12/2002 | Streit et al. | |
| 6,610,648 B2 | 8/2003 | McGee et al. | |
| 6,960,338 B2 | 11/2005 | Li et al. | |
| 7,074,394 B2 | 7/2006 | Li et al. | |
| 7,105,691 B2 | 12/2006 | Holerca et al. | |
| 9,427,386 B2 | 8/2016 | Pan | |
| 2002/0065249 A1 | 5/2002 | Johnson et al. | |
| 2004/0109833 A1 | 6/2004 | Tang et al. | |
| 2004/0198998 A1 | 10/2004 | Holerca et al. | |
| 2006/0204463 A1 | 9/2006 | Tang et al. | |
| 2007/0196308 A1 | 8/2007 | Popoff et al. | |
| 2012/0244099 A1 | 9/2012 | Gale et al. | |
| 2014/0205555 A1 | 7/2014 | Gale et al. | |

FOREIGN PATENT DOCUMENTS

| | | |
|---|---|---|
| GB | 233703 | 12/1925 |
| GB | 2333772 | 8/1999 |
| GB | 2422780 | 8/2006 |
| WO | WO1995030405 | 11/1995 |
| WO | WO2001052804 | 7/2001 |
| WO | WO2005025523 | 3/2005 |
| WO | WO2009075678 | 6/2009 |
| WO | WO2009076591 | 6/2009 |
| WO | WO2011050044 | 4/2011 |

OTHER PUBLICATIONS

Benta Berry Boys, 2013, "Deo Spray Superior Quality," Database GNPD Mintel Accession No. 2094967.
International Search Report and Written Opinion of the International Searching Authority in Application No. PCT/US2014/047347, dated Mar. 25, 2015.
Jaworska et al., 1999, "Environmental Risk Assessment for Trisodium [S,S]-Ethylene Diamine Disuccinate, A Biodegradable Chelator Used in Detergent Applications," Chemosphere 38(15):3597-3625.
Laden, ed., 1999, Ch. 3 "Axillary odor determination, formation, and control," and Ch. 4 "Chemistry of aluminum cholorohydrate and activated aluminum chlorohydrates," *Antiperspirants and Deodorants*, Marcel Dekker, Inc. pp. 59-136.
Oviedo et al., 2003, "EDTA: The Chelating Agent Under Environmental Scrutiny," Quimica Nova 26(6):901-905.

*Primary Examiner* — Ernst V Arnold
*Assistant Examiner* — Kyung S Chang

(57) ABSTRACT

Antiperspirant compositions that incorporate ethylene diamine disuccinate salts as replacements for ethylenediaminetraacetic acid salts.

20 Claims, No Drawings

ANTIPERSPIRANT COMPOSITIONS CONTAINING ETHYLENEDIAMINE DISUCCINATE

BACKGROUND

Ethylenediaminetetraacetic acid (EDTA) and its sodium salts are widely used in the cosmetic and personal care industry as a chelating agent and/or preservation system booster. (Oviendo C., Rodriguez J.; EDTA: The Chelating Agent under Environmental Scrutiny. Quim. Nova (2003). 26 (901-905)). EDTA forms a variety of stable metal complexes with exceptionally high stability constants making it a desirable ingredient to suppress unwanted activity of heavy metals. For example, tetrasodium EDTA is commonly incorporated into water-based antiperspirant formulations to boost preservation system and reduce yellowing caused by free iron cations. Despite its chelating properties, it is desirable to have a more biodegradable chelating agent.

BRIEF SUMMARY

The present disclosure is directed to compositions comprising at least one antiperspirant active comprising aluminum; an ethylenediamine disuccinate salt; and water, wherein the molar ratio of aluminum to ethylenediamine disuccinate (free acid) is 15:1 to 150:1.

Methods of applying the composition to the axillary area of a person are also described.

Uses of ethylenediamine disuccinate salt in an aqueous antiperspirant composition to increase the amount of SEC Peak 4 material are also described.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present inventions are directed to compositions comprising at least one antiperspirant active comprising aluminum, an ethylenediamine disuccinate salt, and water, wherein the molar ratio of aluminum to ethylenediamine disuccinate (free acid) is 15:1 to 150:1.

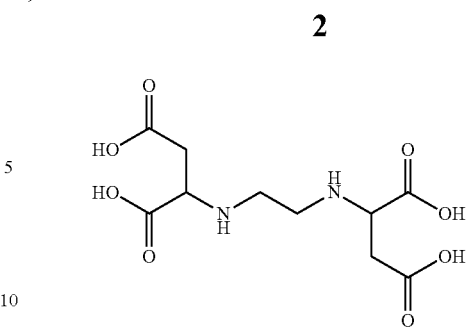

Molecular Structure of Ethylenediamine Disuccinate

In preferred embodiments, these compositions are essentially free of any ethylenediaminetetraacetric acid salts.

In preferred embodiments, the ethylenediamine disuccinate salt is the S,S stereoisomer. In some embodiments, the ethylenediamine disuccinate salt is trisodium ethylenediamine disuccinate.

The antiperspirant actives of the invention include aluminum. The amount of ethylenediamine disuccinate salt in the compositions of the invention will change as the level of aluminum increases or decreases, but in all embodiments, the molar ratio of aluminum to ethylenediamine disuccinate (free acid) is 15:1 to 150:1. In other embodiments, the molar ratio of aluminum to ethylenediamine disuccinate (free acid) is 15:1 to 125:1; 15:1 to 100:1; 15:1 to 75:1; 15:1 to 50:1; or 15:1 to 25:1. In other embodiments, the molar ratio of aluminum to ethylenediamine disuccinate (free acid) is 30:1 to 150:1; 50:1 to 150:1; 75:11 to 150:1; 100:1 to 150:1; or 125:1 to 150:1. In some embodiments, the ratio of aluminum to ethylenediamine disuccinate is about 15:1; 20:1; 25:1; 30:1; 35:1; 40:1; 45:11; 50:1; 55:1; 60:1; 65:1; 70:1; 75:1; 80:1; 85:1; 90:1; 95:1; 100:1; 105:1; 110:1; 115:1; 120:1; 125:1; 130:1; 135:1; 140:1; 145:1; or 150:1.

In preferred embodiments of the invention, the antiperspirant active will comprise aluminum chlorohydrate (ACH). In such embodiments, the ethylenediamine disuccinate salt is present in a weight % ratio of ACH to ethylenediamine disuccinate salt of about 4:1 to about 1:2. In some embodiments, the ethylenediamine disuccinate salt is present in a weight % ratio of anhydrous ACH to ethylenediamine disuccinate salt of about 4:1; 3.5:1; 3:1; 2.5:1; 2:1: 1.5:1; 1:1; 1:1.5; or 1:2.

In compositions of the invention, the ethylenediamine disuccinate salt is present in an amount of from 0.002 weight % to 2.7 weight %, by weight of the composition. In some embodiments, the ethylene disuccinate salt is present in an amount of about 0.002; 0.003; 0.004; 0.005; 0.006; 0.007; 0.008; 0.009; 0.01; 0.02; 0.03; 0.04; 0.05; 0.06; 0.07; 0.08; 0.09; 0.10; 0.11; 0,12; 0.13; 0.14; 0.15; 0.16; 0.17; 0.18; 0.19; 0.20; 0,21; 0.22; 0.23; 0.24; 0.25; 0.26; 0.27; 0,28; 0.29; 0.30; 0.31; 0.32; 0.33; 0.34; 0.35; 0.36; 0.37; 0.38; 0.39; 0.40; 0.41; 0.42; 0.43; 0.44; 0.45; 0.46; 0,47; 0.48; 0.49; 0.50; 0.51; 0.52; 0.53; 0,54; 0.55; 0.56; 0.57; 0.58; 0.59; 0.60; 0.61; 0.62; 0.63; 0.64; 0.65; 0.66; 0.67; 0.68; 0.69; 0.70; 0.71; 0.72; 0.73; 0.74; 0.75; 0.76; 0.77; 0.78; 0.79; 0,80; 0.81; 0.82; 0.83; 0.84; 0.85; 0.86; 0.87; 0.88; 0,89; 0.90; 0.91; 0.92; 0.93; 0.94; 0.95; 0,96; 0.97; 0.98; 0.99; 1.0; 1.1; 1.2; 1.3; 1.5; 1.6; 1.7; 1.8; 1.9; 2.0; 2.1; 2.2; 2.3; 2.4; 2.5; 2.6; or 2.7 weight %.

In compositions of the invention, the ethylenediamine disuccinate salt is present in an amount up to about 0.24 weight %, by weight of the composition. In preferred embodiments, the ethylenediamine disuccinate salt is present in an amount of from 0.03 weight % to 0.24 weight %, by weight of the composition. In other embodiments, the ethylenediamine disuccinate salt is present in an amount of from 0.03 weight % to 0.17 weight %, by weight of the composition. Inother embodiments, the ethylenediamine disuccinate salt is present in an amount of from 0.03 weight % to 0.12 weight %, by weight of the composition. hr other embodiments, the ethylenediamine disuccinate salt is present in an amount of from 0.03 weight % to 0.08 weight %, by weight of the composition. In some embodiments, the ethylenediamine disuccinate salt is present in an amount of about 0.03; 0.08; 0.12; 0.17; or 24 weight %, by weight of the composition. In these embodiments, the antiperspirant active can comprise about 12 weight % of the composition.

Any of the known antiperspirant active materials can be utilized in the compositions of the invention, in any amount. Preferably, the antiperspirant active comprises 0.1 weight % to 25 weight % of the composition, In some embodiments, the antiperspirant active comprises about 0.1; 0.2.; 0.3; 0.4; 0.5; 0.6; 0.7; 0.8; 0.9; 1; 2; 3; 4; 5; 6; 7; 8; 9; 10; 11; 12; 13; 14; 15; 16; 17; 18; 19; 20; 21; 22; 23; 24; or 25 weight % of the composition.

Antiperspirant actives include, but are not limited to, aluminum chlorohydrate, aluminum chloride, aluminum sesquichlorohydrate, aluminum-zirconium hydroxychlorides, complexes or adducts of the above-mentioned active ingredients with glycol, such as propylene glycol (for example, "Rehydrol" II from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for over-the-counter human use (Oct. 10, 1973) can be used.

In other embodiments, the antiperspirant active is an aluminum salt and/or an aluminum-zirconium salt, such as those described above, that are further stabilized by betaine and a calcium salt. More information about betaine and calcium salt stabilized antiperspirant salts can be found in U.S. Patent Application Publication No. 2006/0204463 to Tang et al., which is incorporated herein by reference only for the disclosure of the antiperspirant actives.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al.

In other embodiments, the type of salt of interest, an aluminum zirconium tetrasalt or octasalt free of glycine are used wherein aluminum zirconium salt is stabilized by Betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the Betaine:zirconium mole ratio can be about 0.2:1 to about 3.0:1 (or in other embodiments of about 0.4:1 to about 1.5:1). Another salt that can be used is an aluminum chloride salt buffered by Betaine, wherein the salt has a metal to chloride ratio of 0.9:1 to 1.3:1 (and in other embodiments of about 0.9:1 to about 1.2:1 or about 0.9:1 to about 1.1:1). For the octasaft the Al/Zr atomic ratio is about 6.2:1 to about 10.0:1 and the Betaine:Zr mole ratio is about 0.2:1 to about 3.0:1 (or in other embodiments of about 0.4:1 to about 1.5:1). In one embodiment, in the case of a salt that contains zirconium, the Betaine is incorporated during the synthesis of the salt so as to maximize the stabilizing effect this ingredient has (especially on the zirconium species). Alternatively, it can be post added to a glycine-free salt along with additional active phase ingredients to for a Betaine stabilized active.

Examples of commercially available glycine-free low M:Ci ratio tetrasalts and octasalts include, but are not limited to, REZAL™ AZP 955 CPG and REZAL™ AZP 885 respectively (both from Reheis Chemical Company, Berkeley Heights, N.J.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

In addition to the anti-irritation properties of Betaine, it has also been found that antiperspirant formulations preserve their fragrance stability upon ageing when the Al/Zr salt is used in association with Betaine.

Additionally, the antiperspirant active can be a calcium salt stabilized antiperspirant active. Examples of calcium salt stabilized antiperspirant actives can be found in U.S. Patent Application Publication No. 2006/020.4463, which is incorporated herein by reference only for the disclosure of the calcium salt stabilized antiperspirant actives.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorhydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

Size exclusion chromatography ("SEC") or gel permeation chromatography ("GPC") are methods frequently used for obtaining information on polymer distribution in antiperspirant salt solutions. With appropriate chromatographic columns, generally five distinctive groups of polymer species can be detected in commercial aluminum chlorohydrex ("ACH") and aluminum zirconium glycine ("ZAG") complexes appearing in a chromatogram as peaks 1, 2, 3, 4, and a peak known as "5,6." Peak 1 is the larger Zr species (greater than 60 Angstroms), Peaks 2 and 3 are larger aluminum species. Peak 4 is smaller aluminum species (aluminum oligomers, or small aluminum cluster) and has been correlated with enhanced efficacy for both Al and Al/Zr salts. Peak 5,6 is the smallest aluminum species. Various analytical approaches for characterizing the peaks of ACH and various types of ZAG actives are found in "Antiperspirant Actives-Enhanced. Efficacy Aluminum-Zirconium-Glycine (AZG) Salts" by Dr. Allan H. Rosenberg (Cosmetics and Toiletries Worldwide, Fondots, D.C. ed., Hartfordshire, UK: Aston Publishing Group, 1993, pages 252, 254-256). The polymerization of the antiperspirant actives in aqueous solutions and the correspondent gelation process can be followed by monitoring the molecular weight profile of the polyoxohalides in time by SEC ("size exclusion chromatography"). See WO2009/076591, the entirety of which is incorporated herein by reference.

The relative retention time ("Kd") fir each of these peaks varies depending on the experimental conditions, but the peaks remain relative to each other. For example, an SEC chromatogram can be generated using the following parameters: WATERS® 600 analytical pump and controller, RHEODYNE® 77251 injector, PROTEIN-PAK® 125 (Waters) column, WATERS® 2414 Refractive Index Detector. 5.56 mM nitric acid mobile phase, 0.50 mL/min flow rate, 2.0 microliter injection volume. Date can be analyzed using WATER EMPOWER® software (Waters Corporation, Milford, Mass.). The concentration of the antiperspirant in solution does not affect the retention tie in the machine.

The design of modern antiperspirant salts aims at actives with high levels of low molecular weight Al and Zr species, which is reflected in an SEC trace that has intense Peak 4 and low Peaks 1, 2, 3, and 5/6. Levels of the species corresponding to these peaks are estimated based on the following ratios (or percentages):

$$fPi = \frac{Pi}{\sum Pj} i = 1, 2, 3, 4, 5; j = 2, 3, 4, 5$$

where $f_{Pi}$ is the fraction of peak i, and Pi or Pj are the intensity of peaks Pi or Pj, respectively. The amount of low molecular weight Al species will be correlated with the fraction, $f_{P4}$, or percentage, FP4×100, of SEC-Peak 4. In brief, a preferred antiperspirant salt would have a very low $f_{P1}$, $f_{P2}$, $f_{P3}$, and/or $f_{P5}$, and a high $f_{P4}$.

In some embodiments, the intensity ratio of Peak 4 to Peak 3 is at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or any number up to infinity.

In other embodiments, the percentage of SEC Peak 4 of a total area of Peaks 1, 2, 3, 4, 5, and 6 in the SEC chromatogram is: at least 50%; at least 60%; at least 70%; at least 80%; at least 90%; or 95 to 100% of a total area of Peaks 1, 2, 3, 4, and 5/6 in the SEC chromatogram. in another embodiment, the SEC Peak 4 area is 100%.

The composition can be an aqueous liquid, gel, aerosol, or cream (creams sometimes being included in the term "soft solid"). In the liquid form, the composition can be formulated to be a roll-on product. In the liquid form, the composition can be an oil in water emulsion or a water in oil emulsion. The forms of these products may be suspensions or emulsions. In one embodiment, the composition is an oil in water liquid emulsion. The liquid can be contained in any roll on dispenser that has a ball fir applying the composition to the surface of the skin. For example, the composition of the invention can be an oil-in-water liquid roll-on or a water-in-oil gel or a water-in-oil cream.

Any surfactant that can be used in antiperspirant and/or deodorant compositions can be included. The surfactant can be included in any desired amount. In one embodiment, the amount of surfactant is about 2 to about 12% by weight of the composition. The amount in the composition is based on the as supplied material. In another embodiment, the amount of surfactant is about 3 to about 10% by weight. In one embodiment, when the composition is an oil in water roll-on formula, the amount of surfactant is about 2 to about 5%. In one embodiment, when the composition is a water in oil gel composition, the amount of surfactant is about 3 to about 10%. Examples of the surfactant include, but are not limited to, nonionic surfactants, silicone surfactants, and combinations thereof.

Nonionic surfactants that can be used include, but are not limited to, (a) sorbitan esters and ethoxylated sorbitan esters (tier example PEG-20 sorbitan isostearate, sorbitan monolaurate, polysorbate-20, polysorbate-40, polysorbate-60, polysorbate-80); (b) ethoxylates (for example, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10); (c) ethoxylated adducts (for example, PEG-25 stearate, glyceryl stearate and PEG-100 stearate); (d) PEG esters (for example, PEG-8 oleate, PEG-8 laurate, PEG-8 dilaurate, PEG-12 dilaurate, PEG-80 diisostearate, PEG-40 stearate); (e) propoxylates (for example, PPG-10 butanediol, PPG-50 oleyl ether, PPG-2-ceteareth-9, PPG-3-deceth-3, PPG-5-ceteth-20); (f) ethoxylated modified triglycerides (for example, PEG-20 corn glycerides, PEG-12 palm kernel glycerides); (g) alkylphenol aromatic ethoxylates (for example, dinonylphenol ethoxylate with 9 moles of EO octylphenol ethoxylate with 20 moles of EO, octylphenol ethoxylate with 40 moles of EO); (h) block copolymers that are alkoxylated glycols having ethoxylated and propoxylated segments (for example, POLOXAMER™ 182 and 234, POLOXAMER™ 105 Benzoate, and MEROXAPOL™ 174); and combinations thereof. In one embodiment, the nonionic surfactant is selected so that it has an HLB (hydrophilic-lipophilic balance) value of 8-16 (more particularly 8-12).

In one embodiment, the nonionic surfactant is selected from ethoxylated non-ionic surfactants and propoxylated non-ionic surfactants. Example of these include, but are not limited to Steareth. 2, Steareth 20, and Steareth 21. In an oil in water composition embodiment, a combination of 2 surfactants, one having an HLB value of about 2 to about 8 (such as Steareth 2) and the other having an HLB of about 9 to about 18 (such as Steareth 20 and 21), can be used.

Examples of silicone surfactants can be found in U.S. Pat. No. 6,485,716, which is incorporated herein by reference only for the listing of the silicone surfactants. Suitable silicone surfactants include silicone polyglucosides (fir example, octyl dimethicone ethoxy glucoside) and silicone copolyols having an HLB value (hydrophilic lipophilic balance)≤8. The HLB value may be measured in a variety of ways such as described in conventional references or found listed in tables of data recording such values. It is intended that any type of HLB measurement technique may be used.

In general, silicone copolyols include, but are not limited to, copolyols of the following Formulae I and II. Formula I materials may be represented by:

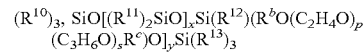

wherein each of $R^{10}$, $R^{11}$, $R^{12}$, and $R^{13}$ may be the same or different and each is chosen from C1-C6 alkyl; $R^b$ is the radical $—C_mH_{2m}—$; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment $—(C_2H_4O)_p—(C_3H_6O)_s—$ has a molecular weight in the range of 200 to 5,000; the segment preferably having fifty to one hundred mole percent of oxyethylene units —(C$_2$H$_4$O)$_p$— and one to fifty mole percent of oxypropylene units —(C$_3$H$_6$O)$_s$—; x has a value of 8 to 400; and y has a value of 2 to 40. Preferably each of R$^{10}$, R$^{11}$, R$^{12}$, and R$^{13}$ is a methyl group; R$^c$ is H; m is preferably three or four whereby the group R$^b$ is most preferably the radical —(CH$_2$)$_3$—; and the values of p and s are such as to provide a molecular weight of the oxyalkylene segment —(C$_2$H$_4$O)$_p$—(C$_3$H$_6$O)$_s$— of between about 1,000 to 3,000. In one embodiment, p and s should each have a value of about 18 to 28. In one embodiment, the silicone copolyol is dimethicone copolyol.

A second siloxane polyether (copolyol) has the Formula II:

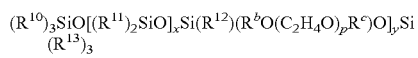

wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers may, in alternate embodiments, take the form of endblocked polyethers in which the linking group R$^b$, the oxyalkylene segments, and the terminating radical R$^c$occupy positions bonded to the ends of the siloxane chain, rather than being bonded to a silicon atom in the siloxane chain. Thus, one or more of the R$^{10}$, R$^{11}$, R$^{12}$, and R$^{13}$ substituents that are attached to the two terminal silicon atoms at the end of the siloxane chain can be substituted with the segment —R$^b$—O—(C$_2$H$_4$O)$_p$—(C$_3$H$_6$O)$_s$—R$^c$ or with the segment —R$^b$O—(C$_2$H$_4$O)$_p$—R$^{.c}$. In some instances, it may be desirable to provide the segment —R$^b$—O—(C$_2$H$_4$O)$_p$—(C$_3$H$_6$O)$_s$—R$^c$ or the segment —R$^b$—O—(C$_2$H$_4$O)$_p$—R$^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING 5225C from Dow Corning, which is a 10% dimethicone copolyol in cyclomethicone; DOW CORNING 2-5185C, which is a 45-49% dimethicone copolyol in cyclomethicone; SILWET L-7622 from Witco; ABIL EM97 from Goldschmidt, which is a 85% dimethicone copolyol icy D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING 2-5185 can be used in one embodiment.

In one embodiment, 0.5-5 weight % (particularly 1.0-2.0%) of a 10% silicone copolyol such as dimethicone copolyol in cyclomethicone mixture may be used, wherein the amount of mixture added is selected so that the level of silicone copolyol in the composition is in the range of 0.05-0.5% (particularly 0.1%) (for example, 1% of a 10% dimethicone copolyol in cyclomethicone mixture).

When the composition contains a deodorant active, any known deodorant active can be used. Examples of deodorant active include, but are not limited to antimicrobial actives, alcohols, 2,4,4'-trichloro-2'-hydroxy diphenyl ether (Triclosan), octoxyglycerin (SENSIVA™ SC 50), benzethonium chloride, polyhexamethylene biguanides, triethylcitrate, 2-amino-2-methyl-1-propanol (AMP), cetyltrimethylammomium bromide, cetyl pyridinium chloride, bactericides, and bacteriostats.

In certain embodiments, the composition may also contain as an optional ingredient at least one malodor counteracting alpha, beta-unsaturated ester or mixtures of such materials. In certain embodiments, the level of malodor counteracting composition to deliver a perceivable odor control benefit when delivered from an antiperspirant and/or deodorant composition is about 0.05 to about 0.45 weight % based on the entire composition. The alpha, beta-unsaturated ester malodor counteracting materials are incorporated within the oil phase of an antiperspirant composition. Example of these malodor counteracting components can be found in U.S. Pat. Nos. 6,610,648 and 6,495,097, which are incorporated herein only for their disclosure of the alpha, beta unsaturated esters. For example, in this invention the odor neutralizing alpha, beta unsaturated ester mixture demonstrates unexpected stability in antiperspirant compositions containing low metal:chloride (M:Cl) ratio salts free of glycine. Examples of the alpha, beta unsaturated ester can be found in WO2005/025523, which was filed in the United States as U.S. application Ser. No. 10/571,488, both of which are incorporated herein by reference to the extent that they do not conflict with the disclosure in this specification.

Examples of the alpha, beta unsaturated ester include, but are not limited to:

(1) 3-phenyl-2-propenoic acid alkyl esters wherein R$^1$ is a substituent on the benzene ring and is chosen from an alkyl, an alkoxy, an aryl, or a substituted aryl. In certain embodiments, R$^1$ is chosen from H, a C$_1$ to C$_8$ alkyl, a C$_1$ to C$_8$ alkoxy, or an aryl; and R$^2$ is a subsistent group replacing the carboxylic acid hydrogen to form the ester where R$^2$ has greater than 6 carbon atoms, an aryl, or a substituted aryl group, in certain embodiments R$^2$ is a C$_6$ to C$_{12}$ alkyl or is a benzyl group; and (2) an ester of fumaric or maleic acid having linear ester carbon chains from 3-9 carbons, for example dihexyl fumarate;

(3) e-phenyl propenoic acid ester chosen from octyl methoxy cinnamate, phenylethyl cinnamate, benzyl cinnamate; and (4) an aliphatic unsaturated ester, such as dihexyl fumarate.

The composition may contain additional materials that are included in antiperspirant and/or deodorant compositions. Examples include, but are not limited to monohydric alcohols, fragrances, and preservatives.

When water is present, for example in a liquid roll-on composition, the amount of water in the composition is the amount to make a 100% by weight composition after all of the materials, including any optional materials, are added to the composition. In certain embodiments, the amount of water is at least about 20%, 30%, 40%, 50%, 60%, 70%, 80%, or 85% by weight of the composition.

The total solids of the composition is the amount of non-volatile materials in the composition. The percent solids is measured by a CEM Smart System moisture solids analyzer which uses microwave energy to dry the samples. In one embodiment, the total solids is less than about 25%. In another embodiment, the total solids is less than about 20%.

Compositions of the invention can be used by applying the composition to the axillary area of a person.

EXAMPLES

Materials:
ACH103 (aluminium chlorohydrate) Powder25.4% Al
EDTA 62%-$Na_4$ Dihydrate
Trisodium Ethylene Diamine N,N Disuccinate (30.1% Free Acid)

Samples were freshly prepared, according to amounts shown in Tables 1-2, with reagents used as received by manufacturer. Following preparation of 12% ACH103 solution, chelating agents were weighed, in a scintillation vial, with a laboratory scale (±0.0001 g). ACH solution was added to the scintillation vials to reach a final weight of 10 g. Samples were placed in a sonicator for 5 minutes to allow complete dissolution then aged in a 50° C. oven for 3 days. Peak 4 intensity is used herein as indicator of efficacy. SEC is conducted as described above.

Tetrasodium EDTA is currently formulated into roll-on UAP products at 0.25% for preservative boosting and chelating function; therefore, 0.25% tetrasodium EDTA was used as control. Although EDDS was added as 30.1% solution (according to CoA), the discussion refers only to the actual concentration of EDDS. As shown in Table 3, EDDS demonstrated enhanced Peak 4 intensity at 0.03%, 0.18%, and 0.12%. At 0.24%, the control (0.25% tetrasodium EDTA) exhibited 7% more Peak 4. See Table 3. According to the best fit equation of the data in Table 3, peak 4 intensities will be equal to that of the control at 0.17% EDDS solution.

TABLE 1

ACH103 Stock Solution Preparation

| Theoretical | | | Experimental | | |
|---|---|---|---|---|---|
| % ACH (Anh.) | ACH* (g) | Total (g) | % ACH (Anhydrous) | ACH* (g) | Total (g) |
| 12 | 8.7874 | 60 | 12 | 8.7882 | 60.0145 |

*ACH contains 25.4% Al and 82% anhydrous content

TABLE 2A

Sample Preparation

| | Theoretical | | |
|---|---|---|---|
| Sample | Chelator (g) | ACH Sol (g) | Total (g) |
| 0.25% Na4-EDTA | 0.025 | 9.975 | 10 |
| 0.1% EDDS* | 0.01 | 9.99 | 10 |
| 0.3% EDDS* | 0.02 | 9.98 | 10 |
| 0.4% EDDS* | 0.04 | 9.96 | 10 |
| 0.8% EDDS* | 0.08 | 9.92 | 10 |

*EDDS was added as 30.1% solution

TABLE 2B

Sample Preparation

| | Experimental | | | | |
|---|---|---|---|---|---|
| Sample | % Chelator | wt. % EDDS | Chelator (g) | ACH Sol (g) | Total (g) |
| 0.25% Na4-EDTA | 0.25 | n/a | 0.0250 | 9.9931 | 10.0181 |
| 0.1% EDDS* | $0.11^a$ | 0.03 | 0.0110 | 10.0095 | 10.0205 |
| 0.3% EDDS* | $0.28^b$ | 0.08 | 0.0282 | 9.9609 | 9.9891 |
| 0.4% EDDS* | $0.38^c$ | 0.12 | 0.0382 | 9.9424 | 9.9806 |
| 0.8% EDDS* | $0.78^d$ | 0.24 | 0.0784 | 9.9145 | 9.9929 |

*EDDS was added as 30.1% solution (CoA)

TABLE 3

SEC Peak Areas

| Sample | Peak 4 Area | % Change* |
|---|---|---|
| 0.25% Na4-EDTA | 454395 | 0 |
| 0.1% EDDS* | 514419 | 13.2 |
| 0.3% EDDS* | 492300 | 8.3 |
| 0.4% EDDS* | 464803 | 2.3 |
| 0.8% EDDS* | 422651 | −7.0 |

*% Change is ΔPeak 4 compared to Na4-EDTA (control)

What is claimed is:

1. A composition comprising:
    at least one antiperspirant active comprising aluminum;
    an ethylenediamine disuccinate salt; and
    water;
    wherein the molar ratio of aluminum to ethylenediamine disuccinate is 15:1 to 150:1; and
    wherein the ethylenediamine disuccinate salt is present in an amount of from 0.03% to 0.12% by weight of the composition.

2. The composition of claim 1, wherein the molar ratio of aluminum to ethylenediamine disuccinate is 15:1 to 100:1.

3. The composition of claim 1, wherein the molar ratio of aluminum to ethylenediamine disuccinate is 15:1 to 50:1.

4. The composition of claim 1, wherein the molar ratio of aluminum to ethylenediamine disuccinate is 15:1 to 25:1.

5. The composition of claim 1, wherein the molar ratio of aluminum to ethylenediamine disuccinate is 30:1 to 150:1.

6. The composition of claim 1, wherein the molar ratio of aluminum to ethylenediamine disuccinate is 75:1 to 150:1.

7. The composition of claim 1, wherein the molar ratio of aluminum to ethylenediamine disuccinate is 125:1 to 150:1.

8. The composition of claim 1, wherein the ethylenediamine disuccinate salt is trisodium ethylenediamine disuccinate.

9. The composition of claim 1, having a size exclusion chromatography (SEC) Peak 4 area of at least 50% of a total area of Peaks 1, 2, 3, 4, 5, and 6 in the SEC chromatogram.

10. The composition of claim 1, having an SEC Peak 4 area of at 95% to 100% of a total area of Peaks 1, 2, 3, 4, 5, and 6 in the SEC chromatogram.

11. The composition of claim 1, exhibiting an SEC chromatogram having an SEC Peak 4 to Peak 3 intensity ratio of at least 2.

12. The composition of claim 1, exhibiting an SEC chromatogram having an SEC Peak 4 to Peak 3 intensity ratio of at least 20.

13. The composition of claim 1, exhibiting an SEC chromatogram having an SEC Peak 4 to Peak 3 intensity ratio of at least 100.

14. The composition of claim 1 further comprising a surfactant.

15. The composition of claim 14, wherein the surfactant is present in an amount of about 2 to about 12% by weight of the composition.

16. The composition of claim 1 further comprising a deodorant active.

17. The composition of claim 1, wherein the composition has a total solids content of about 25 weight % or less.

18. The composition of claim 1, wherein the water is present in an amount that is at least about 20 weight % by weight of the composition.

19. The composition of claim 1 further comprising an odor neutralizing alpha, beta unsaturated ester mixture.

20. A method comprising applying the composition of claim 1 to the axillary area of a person.

* * * * *